US00PP13787P29

(12) United States Plant Patent
Kerley

(10) Patent No.: US PP13,787 P2
(45) Date of Patent: May 6, 2003

(54) PETUNIA PLANT NAMED 'KERCAN'

(76) Inventor: Priscilla G. Kerley, Bethany, 49 Station Road, Over, Cambridge, CB4 5NJ (GB)

( * ) Notice: Subject to any disclaimer, the term of this patent is extended or adjusted under 35 U.S.C. 154(b) by 0 days.

(21) Appl. No.: 10/051,913

(22) Filed: Jan. 17, 2002

(51) Int. Cl.[7] ..... A01H 5/00
(52) U.S. Cl. ..... Plt./356

(58) Field of Search ..... Plt./356

*Primary Examiner*—Bruce R. Campell
*Assistant Examiner*—Susan B. McCormick
(74) *Attorney, Agent, or Firm*—C. A. Whealy

(57) ABSTRACT

A new and distinct cultivar of Petunia plant named 'Kercan', characterized by its outwardly spreading, cascading and uniform plant habit; compact growth habit; early flowering habit; numerous large double flowers that are red purple in color; and good garden performance.

2 Drawing Sheets

BOTANICAL CLASSIFICATION/CULTIVAR DESIGNATION

*Petunia×hybrida* cultivar Kercan.

BACKGROUND OF THE INVENTION

The present Invention relates to a new and distinct cultivar of Petunia plant, botanically known as *Petunia×hybrida*, and hereinafter referred to by the cultivar name Kercan.

The new Petunia is a product of a planned breeding program conducted by the Inventor in Over, Cambridge, United Kingdom. The objective of the breeding program is to create new cascading Petunias with numerous double flowers with attractive flower colors.

The new Petunia originated from a cross made by the Inventor in August, 1998 of an unidentified proprietary seedling selection of Petunia with single flowers, not patented, as the female, or seed, parent with an unidentified proprietary seedling selection of Petunia with salmon pink-colored flowers, not patented, as the male, or pollen, parent. The new Petunia was selected as a single plant from the resulting progeny in July, 1999 in Over, Cambridge, United Kingdom on the basis of its double and numerous red purple-colored flowers.

Asexual reproduction of the new cultivar by terminal vegetative cuttings since August, 1999, taken in Over, Cambridge, United Kingdom has shown that the unique features of this new Petunia are stable and reproduced true to type in successive generations.

SUMMARY OF THE INVENTION

Plants of the cultivar Kercan have not been observed under all possible environmental conditions. The phenotype may vary somewhat with variations in environment such as temperature, light intensity and daylength without, however, any variance in genotype.

The following traits have been repeatedly observed and are determined to be the unique characteristics of 'Kercan'. These characteristics in combination distinguish 'Kercan' as a new and distinct cultivar:

1. Outwardly spreading, cascading and uniform plant habit.

2, Compact growth habit.

3. Early flowering habit.

4. Numerous large double flowers that are red purple in color.

5. Good garden performance.

Plants of the new Petunia differ from plants of the female parent, an unidentified red purple-colored single-flowered selection, in the following characteristics:

1. Plants of the new Petunia are more compact and not as pendulous as plants of the female parent.

2. Plants of the new Petunia have larger flowers than plants of the female parent.

3. Plants of the new Petunia have double flowers whereas plants of the female parent have single flowers.

Plants of the new Petunia differ from plants of the male parent, an unidentified salmon pink-colored double-flowered Petunia selection, in the following characteristics:

1. Plants of the new Petunia are more cascading and not as upright as plants of the male parent.

2. Plants of the new Petunia have red purple-colored flowers whereas plants of the male parent have salmon pink-colored flowers.

Plants of the new Petunia can be compared to plants of the cultivar Cobink, disclosed in U.S. Plant Pat. No. 12,012. In side-by-side comparisons conducted in Over, Cambridge, United Kingdom, plants of the new Petunia differed from plants of the cultivar Cobink in the following characteristics:

1. Plants of the new Petunia had smaller and paler green-colored foliage than plants of the cultivar Cobink.

2. Plants of the new Petunia flowered about five days earlier than plants of the cultivar Cobink.

3. Plants of the new Petunia had larger flowers than plants of the cultivar Cobink.

4. Flower color of plants of the new Petunia was more uniform than flower color of plants of the cultivar Cobink.

5. Plants of the new Petunia had larger sepals than plants of the cultivar Cobink.

BRIEF DESCRIPTION OF THE PHOTOGRAPHS

The accompanying colored photographs illustrate the overall appearance of the new Petunia, showing the colors as true as it is reasonably possible to obtain in colored reproductions of this type. Colors in the photographs may differ slightly from the color values cited in the detailed botanical description which accurately describe the colors of the new Petunia.

The photograph on the first sheet comprises a side perspective view of a typical flowering plant of 'Kercan' grown in a 20-cm hanging basket container.

The photograph on the second sheet comprises a close-up view of typical flowers of 'Kercan'. Plants used in the photographs were about 28 weeks from planting.

DETAILED BOTANICAL DESCRIPTION

The aforementioned photographs and following observations and measurements describe plants grown in Over, Cambridge, United Kingdom, in a plastic-covered greenhouse during the late summer and autumn with day temperatures ranging from 18 to 30° C. and night temperatures ranging from 14 to 20° C. After planting rooted cuttings, plants were pinched one time. Plants used for the description were about 14 weeks from planting. Color references are made to The Royal Horticultural Society Colour Chart, 1995 edition, except where general terms of ordinary dictionary significance are used.

Botanical classification: *Petunia×hybrida* cultivar Kercan.

Parentage:

*Female parent.*—Unidentified proprietary seedling selection of *Petunia×hybrida*, not patented.

*Male parent.*—Unidentified proprietary seedling selection of *Petunia×hybrida*, not patented.

Propagation:

*Type cutting.*—Terminal vegetative cuttings.

*Time to initiate roots.*—Summer: About 10 days at 21° C. Winter: About 14 days at 21° C.

*Time to produce a rooted young plant.*—Summer: About 30 days at 20° C. Winter: About 45 days at 20° C.

*Root description.*—Fine, fibrous.

*Rooting habit.*—Freely branching.

Plant description:

*Form.*—Annual flowering plant; indeterminate; initially upright, then outwardly spreading and cascading; uniform; compact growth habit. Freely branching habit with about six lateral branches developing after pinching (removal of terminal apices).

*Plant height.*—About 25 cm.

*Plant diameter.*—About 40 cm.

*Vigor.*—Moderate.

*Lateral branches.*—Length: About 34 cm. Diameter: About 4.4 mm. Internode length: About 2.8 cm. Texture: Pubescent. Color: 146C to 146D.

*Foliage description.*—Arrangement: Alternate before flowering; opposite after flowers develop; simple. Length: About 5.4 cm. Width: About 3.25 cm. Shape: Broadly elliptic. Apex: Slightly acute to slightly blunt. Base: Acute. Margin: Entire. Texture, upper and lower surfaces: Pubescent. Venation pattern: Pinnate, arcuate. Color: Developing leaves, upper surface: 146B. Developing leaves, lower surface: 146B to 146C. Fully expanded leaves, upper surface: 137C. Fully expanded leaves, lower surface: 146C. Venation, upper surface: 137C. Venation, lower surface: 146C. Petiole length: About 10.25 mm. Petiole diameter: About 2.8 mm. Petiole color: 144C to 145B to 145C.

Flower description:

*Flower type and habit.*—Double salverform flowers; flowers face mostly upward or outward; axillary. Very freely flowering habit, typically one flower per node; indeterminate.

*Natural flowering season.*—Long day responsive; long flowering period, spring until frost in the autumn; flowering continuous during this period. Plants start flowering about 39 days after planting rooted cuttings. Flowers persistent.

*Flower longevity on the plant.*—About one week.

*Fragrance.*—Very faint, sweet.

*Flower size.*—Diameter: About 7 cm. Tube length: About 2 cm. Throat diameter, distal end: About 2.2 cm. Tube diameter, proximal end: About 7 mm.

*Flower buds (at stage of showing color).*—Length: About 3.2 cm. Shape: Elongated oblong with ruffled apices. Color: 186C to 186D, venation, 146C.

*Corolla.*—Quantity/arrangement: About five fused outer petals in a single whorl, funnelform; interior to the outer whorl, about nine progressively smaller petaloids, variable in size. Petal length from throat: About 3.5 cm. Petal width: About 3.2 cm. Petal/petaloid shape: Roughly spatulate. Petal/petaloid apex: Very slightly mucronate; reflexed. Petal/petaloid margin: Entire; ruffled. Petal/petaloid texture: Smooth, velvety. Color: Petals/petaloids, upper surface, when opening: 66B. Petals/petaloids, lower surface, when opening: 66D. Petals/petaloids, upper surface, fully opened: 66D; color does not fade with subsequent development. Petals/petaloids, lower surface, fully opened: 65B to 68D. Flower throat (inside): Close to 66D. Flower tube (outside): 69B to 65D. Venation, upper petal/petaloid surface: 66A to 66B. Venation, lower petal/petaloid surface: 200C to 200D. Venation, throat: Close to 66A to 66B. Venation, tube: 148A.

*Sepals.*—Arrangement/appearance: Single whorl of five sepals fused at base, star-shaped. Length: About 1.4 cm. Width: About 4 mm. Shape: Strap-like; elongate. Apex: Acute. Margin: Entire, pubescent. Texture, both surfaces: Pubescent, glandular. Color: Upper surface: Darker than 144A. Lower surface: 144A to 144B.

*Peduncles.*—Length: About 2.75 mm. Width: Less than 1 mm. Angle: About 35 to 45° from the stem. Strength: Strong. Texture: Pubescent. Color: 144A.

*Reproductive organs.*—Stamens: Quantity per flower: About 33 stamens. Anther shape: Ovoid. Anther length: Less than 1 mm. Anther color: Close to 155D. Pollen amount: Abundant. Pollen color: Close to 158A. Pistils: Quantity per flower: Usually none, occasionally one, sterile and mostly malformed.

*Seed/fruit.*—Seed and/or fruit production has not been observed to date.

Disease/pest resistance: Plants of the new Petunia have not been noted to be resistant to pathogens or pests common to Petunia.

Garden performance: Plants of the new Petunia have been observed to have good garden performance. Plants of the new Petunia have been noted to tolerate temperatures from 0 to 35° C. and have excellent tolerance to rain and wind.

It is claimed:

1. A new and distinct cultivar of Petunia plant named 'Kercan', as illustrated and described.

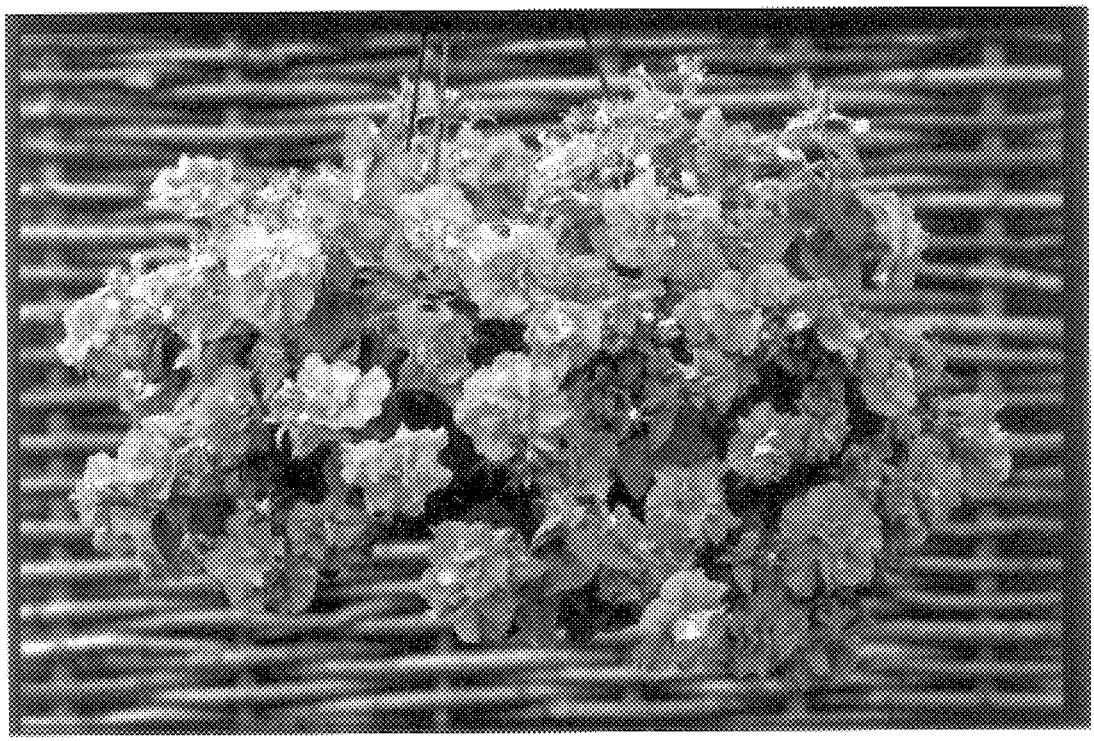

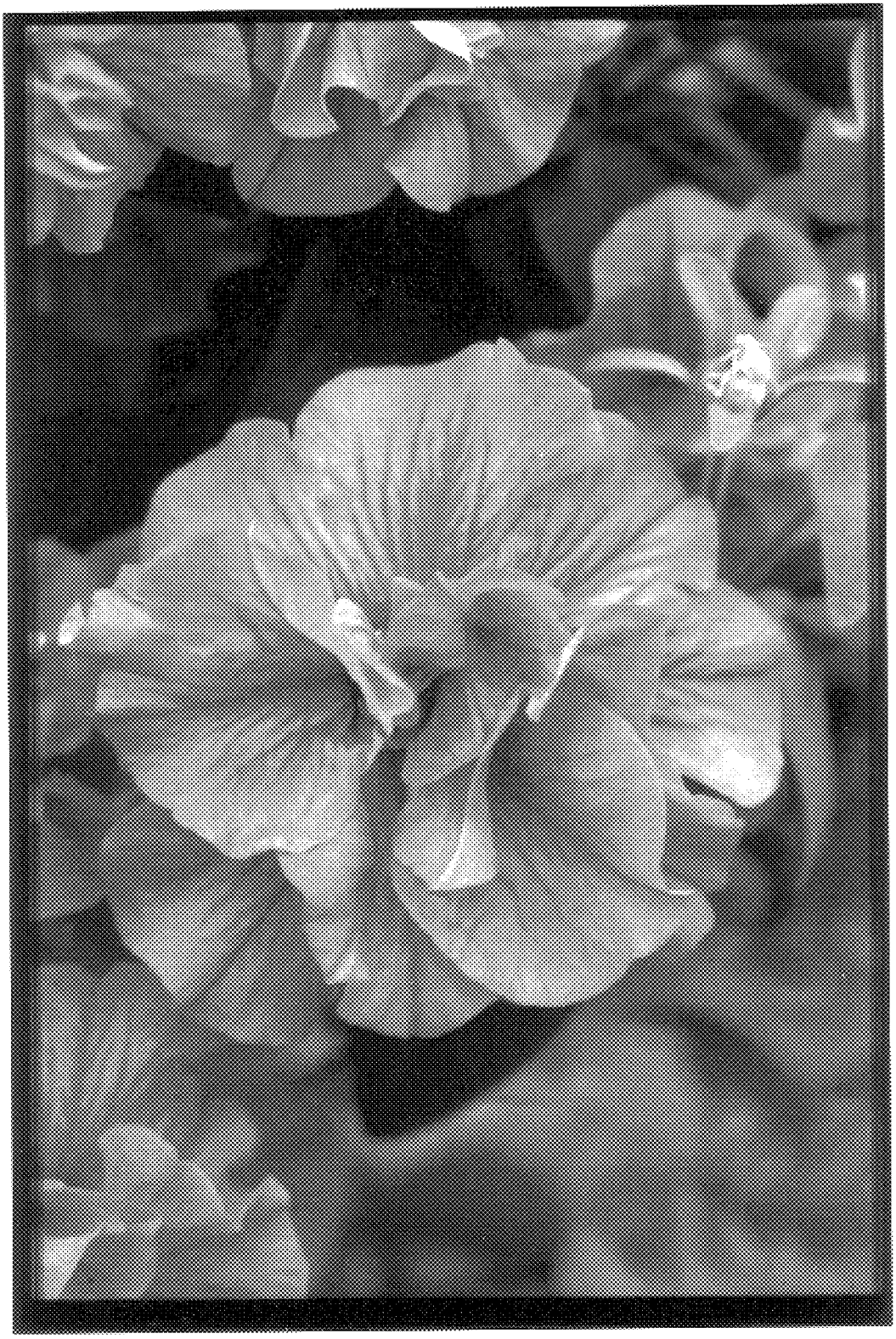

* * * * *